(12) United States Patent
Umehara et al.

(10) Patent No.: US 9,950,133 B2
(45) Date of Patent: Apr. 24, 2018

(54) HEAT AND MOISTURE EXCHANGER

(71) Applicants: Toray Medical Co., Ltd., Tokyo (JP);
 Toray Fine Chemicals Co., Ltd.,
 Tokyo (JP)

(72) Inventors: Tsuguaki Umehara, Tokyo (JP);
 Hiroyuki Fukuda, Matsuyama (JP);
 Masato Mutoh, Fujisawa (JP);
 Takehiko Hirabara, Osaka (JP);
 Yusuke Shobu, Tokyo (JP); **Hideyuki
 Takeshige**, Tokyo (JP)

(73) Assignees: Toray Medical Co., Ltd. (JP); **Toray
 Fine Chemicals Co., Ltd.** (JP)

( * ) Notice: Subject to any disclaimer, the term of this
 patent is extended or adjusted under 35
 U.S.C. 154(b) by 684 days.

(21) Appl. No.: 14/384,768

(22) PCT Filed: Mar. 8, 2013

(86) PCT No.: PCT/JP2013/056396
 § 371 (c)(1),
 (2) Date: Sep. 12, 2014

(87) PCT Pub. No.: WO2013/137125
 PCT Pub. Date: Sep. 19, 2013

(65) Prior Publication Data
 US 2015/0053368 A1   Feb. 26, 2015

(30) Foreign Application Priority Data
 Mar. 13, 2012 (JP) .................. 2012-055592

(51) Int. Cl.
 *A61M 16/10* (2006.01)
 *F28D 20/00* (2006.01)
 *F28D 17/02* (2006.01)

(52) U.S. Cl.
 CPC .... *A61M 16/1075* (2013.01); *A61M 16/1045*
 (2013.01); *F28D 17/02* (2013.01);
 (Continued)

(58) Field of Classification Search
 CPC .................. A61M 16/1045; F28D 9/04; F28D
 7/02–7/04; F28D 2020/0017;
 (Continued)

(56) References Cited

U.S. PATENT DOCUMENTS 4,189,330 A * 2/1980 Strindehag .............. C23C 22/66
 148/272
4,200,441 A * 4/1980 Honmann .............. F24F 3/1423
 165/10

(Continued)

FOREIGN PATENT DOCUMENTS

JP 59-49776 3/1984
JP 59-49776 A 3/1984
(Continued)

OTHER PUBLICATIONS

Extended European Search Report dated Sep. 14, 2015, from corresponding European Application No. 13761175.2.

*Primary Examiner* — Tan-Uyen (Jackie) T Ho
*Assistant Examiner* — Joseph D Boecker
(74) *Attorney, Agent, or Firm* — DLA Piper LLP (US)

(57) ABSTRACT

A heat and moisture exchanger includes: a heat and moisture exchanger material formed by coiling a strip-shaped porous body, the porous body having a plurality of slits formed therein that are arranged along the lengthwise direction, into a spirally-wound shape with the slits facing radially outwardly; and a housing that accommodates the heat and moisture exchanger material. Such a structure for an HME makes it possible to reduce pressure loss and improve moisture retention capabilities by means of a relatively (Continued)

simple structure, thereby allowing the inexpensive provision of an HME that lowers the burden on a patient.

17 Claims, 8 Drawing Sheets

(52) U.S. Cl.
CPC ..... *F28D 20/0056* (2013.01); *A61M 16/1055* (2013.01); *A61M 2207/00* (2013.01); *A61M 2209/02* (2013.01); *F28D 2020/0017* (2013.01)

(58) Field of Classification Search
CPC ... F28D 17/02; B01D 29/0022; B01D 29/016; B01D 29/073; B01D 27/06; B01D 27/07; B01D 46/403; B01D 63/10; B01D 63/103
USPC ...................................................... 261/112.1
See application file for complete search history.

(56) References Cited

U.S. PATENT DOCUMENTS

| | | | | |
|---|---|---|---|---|
| 4,391,616 | A * | 7/1983 | Imamura | B01D 53/261 95/92 |
| 5,462,048 | A * | 10/1995 | Lambert | A61M 16/1045 128/201.13 |
| 5,701,891 | A * | 12/1997 | Groenke | A61M 16/1045 128/201.13 |
| 5,771,707 | A * | 6/1998 | Lagace | F24F 3/1423 165/8 |
| 5,906,201 | A * | 5/1999 | Nilson | A61M 16/1045 128/203.16 |
| 6,007,750 | A * | 12/1999 | Firgo | C08J 9/103 264/344 |
| 6,695,044 | B1 * | 2/2004 | Symonds | B01J 19/249 165/166 |
| 6,769,430 | B1 * | 8/2004 | Carlsen | A61M 16/0463 128/201.13 |
| 6,892,795 | B1 * | 5/2005 | Steele | F23L 15/02 165/10 |
| 7,347,203 | B2 * | 3/2008 | Marler | A61M 16/08 128/200.14 |
| 8,590,606 | B2 * | 11/2013 | Arai | F24F 12/006 165/166 |
| 2003/0118781 | A1 * | 6/2003 | Insley | B01D 39/1607 428/172 |
| 2006/0278089 | A1 * | 12/2006 | Theilow | B01D 53/263 96/290 |
| 2010/0071886 | A1 * | 3/2010 | Shikazono | F28F 1/32 165/151 |
| 2011/0017438 | A1 * | 1/2011 | Huazhao | F25B 39/028 165/174 |
| 2011/0297152 | A1 * | 12/2011 | Duveen | A61M 16/06 128/203.29 |
| 2012/0199330 | A1 * | 8/2012 | Maurer | F25B 39/028 165/168 |
| 2012/0205081 | A1 * | 8/2012 | Terai | F28D 9/0025 165/133 |

FOREIGN PATENT DOCUMENTS

| | | |
|---|---|---|
| JP | 59-88159 | 5/1984 |
| JP | 59-88159 A | 5/1984 |
| JP | 61-280871 | 12/1986 |
| JP | 61-280871 A | 12/1986 |
| JP | 2006-136461 A | 6/2006 |
| WO | 94/02192 | 2/1994 |
| WO | 97/15344 | 5/1997 |
| WO | 97/36742 | 10/1997 |

* cited by examiner (A)

(B)

(C)

VENTILATOR SIDE

PATIENT SIDE (A)

(B)

(C)

(A)

(B)

HEAT AND MOISTURE EXCHANGER

TECHNICAL FIELD

This disclosure relates to a heat and moisture exchanger to maintain the temperature and humidity of inhalation air in an appropriate state when a ventilator or the like is used for a patient.

BACKGROUND

As a device to moisturize dry inhalation air supplied from an apparatus such as an anesthesia apparatus or a ventilator when using the apparatus, a heat and moisture exchanger is previously known in which a heat and moisture exchange material to capture water vapor contained in a patient's exhalation air and moisturizing inhalation air by the water vapor is provided. Such a passive device which is small, lightweight and inexpensive compared to active devices having a humidifier or heat source is less prone to problems that may potentially lead to a medical accident such as moisture shortage caused by a mistake in operating the humidifier or heat source, and is accordingly widely used in medical fields.

With regard to the heat and moisture exchanger, from the viewpoint of reducing the burden on the patient it is required to add sufficient moisture to inhalation air to maintain humidity in the inhalation air, and to keep pressure loss to be small and uniform. Further, because it does not have a mechanism to supply moisture from outside, it is important to have a moisture retention capability to capture moisture contained in inhalation air. For example, in JP-A-2006-136461, disclosed is a moisture exchanger for respiratory gas in which a supplemental heat and moisture accumulator made of corrugated paper is positioned in an opening portion on the patient side, the supplemental heat and moisture accumulator containing a hygroscopic substance such as glycols and calcium chloride.

However, in the moisture exchanger for respiratory gas described in JP '461, there is a fear that pressure loss may increase compared to conventional ones because the supplemental heat and moisture accumulator is positioned therein and, although the moisture retention capability is improved, the ventilation property is not adequately secured. Further, because the moisture exchanger requires additional processes such as a process of accommodating the supplemental heat and moisture accumulator in a housing and a process to make a hygroscopic substance be contained in the supplemental heat and moisture accumulator, it is difficult to suppress an increase in manufacturing cost.

Accordingly, it would be helpful to provide a heat and moisture exchanger of reducing a burden on a patient at low cost by a relatively simple structure that can reduce pressure loss and improve moisture retention capability.

SUMMARY

We provide a heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material.

We also provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein the slits are formed on a surface of the porous member at a slit depth ratio of 40-95%.

We further provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein the slits are formed in a shape intersecting with the longitudinal direction.

We further provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein the slits are formed in a shape intersecting with the longitudinal direction, and wherein the slits are formed in the shape intersecting with the longitudinal direction at an intersection angle of 50-70°.

We further provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein the slits are formed in a zigzag shape.

We further provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein a water absorption ratio of the porous member is 500% or higher.

We further provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein the porous member is made of a cellulose sponge.

We further provide the heat and moisture exchanger including a heat and moisture exchange material formed into a spirally-wound shape with a plurality of slits facing radially outwardly by coiling a strip-shaped porous member having the slits that are arranged along a longitudinal direction of the porous member, and a housing that accommodates the heat and moisture exchange material, wherein the heat and moisture exchanger is used with a ventilator connected thereto.

BRIEF DESCRIPTION OF THE DRAWINGS

FIG. 1(A) is a diagrammatic oblique view, FIG. 1(B) is a partially enlarged oblique view, and FIG. 1(C) is a partially enlarged plan view.

FIG. 3(A) is a diagrammatic sketch showing a structure of this heat and moisture exchanger, FIG. 3(B) is a diagrammatic oblique view, and FIG. 3(C) is a diagrammatic vertical cross-sectional view.

FIG. 4(A) is a diagrammatic sketch showing a structure of this heat and moisture exchanger, FIG. 4(B) is a diagrammatic oblique view, and FIG. 4(C) is a diagrammatic vertical cross-sectional view.

FIG. 6(A) shows a measurement result of absolute humidity on ventilator side, and FIG. 6(B) shows a measurement result of absolute humidity on patient side.

REFERENCE SIGNS LIST

Figure 1:
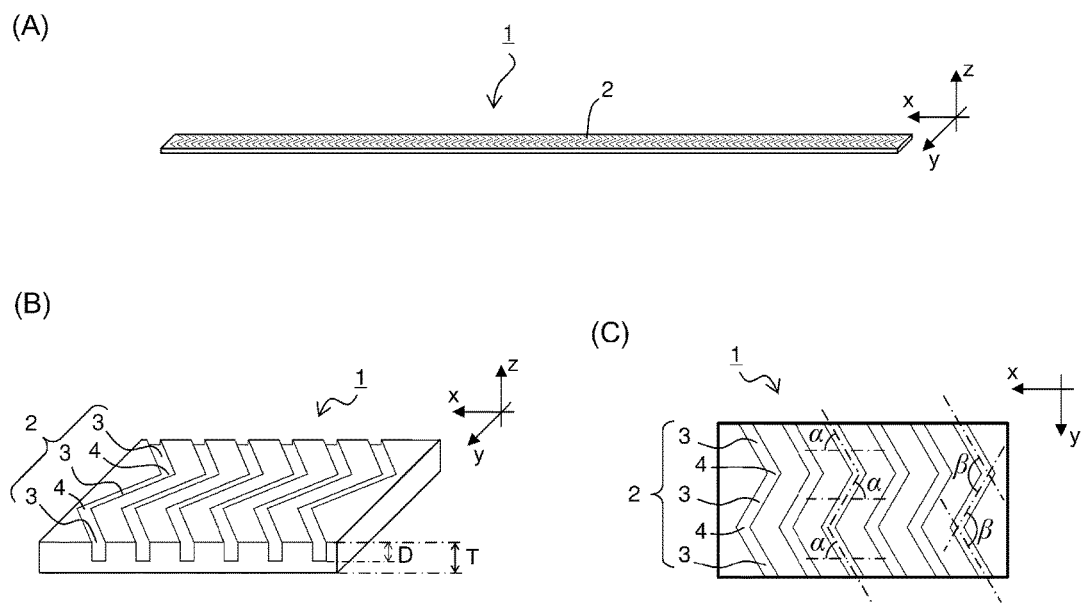
FIG. 1 shows a porous member used in a heat and moisture exchanger.

1: porous member
2: slit
3: straight part
4: bend
4a: curve
5: heat and moisture exchange material
6: lid member
7: casing member
8: housing
9: heat and moisture exchanger
10: bacteria filter
11: ventilator
12a, 12b: thermo-hygrometer
13: check valve
14: test lung
15: active humidifier
16: moisturizing chamber
17: heat wire
18: circuit
20: raw material
21: sheet
22: heat-compressed sheet
23: heat-compressed porous member

DETAILED DESCRIPTION

We provide a heat and moisture exchanger comprising: a heat and moisture exchange material formed into a spirally-wound shape with a plurality of slits facing radially outward by coiling a strip-shaped porous member having the slits that are arranged along a longitudinal direction of the porous member; and a housing to accommodate the heat and moisture exchange material.

In such a heat and moisture exchanger, because the heat and moisture exchange material is formed by coiling a strip-shaped porous member in which a plurality of slits are formed, the slits serve as flow paths for exhalation and inhalation, and it is thus possible to reduce pressure loss to a low level and exhibit an excellent moisture retention capability and a moisturizing capability obtained by the porous member. Further, because the amount of pressure loss and the moisture retention capability of the heat and moisture exchange material can be controlled by changing the shape of the slits, it is possible to design and manufacture the heat and moisture exchange material with ease in a manner appropriate to its use, and it is thus possible to meet a wide variety of performance requirements with flexibility. Further, because the heat and moisture exchanger is configured with a simple structure in which substantially only a heat and moisture exchanger material is accommodated in a housing, it is possible to simplify the manufacturing process and reduce the manufacture cost to a low level. However, in the housing of the heat and moisture exchanger, a member other than the heat and moisture exchange material may be accommodated. For example, it is possible to position a bacteria filter in the housing on ventilator side to prevent inhalation air from pollution.

It is preferred that the slits are formed on a surface of the porous member at a slit depth ratio of 40-95%. The slit depth ratio is, when the thickness of the porous member is referred to as T and the depth of a slit is referred to as D, a ratio D/T (%) of a ratio of the depth D to the thickness T. If the slit depth ratio is less than 40%, because the flow paths for exhalation and inhalation become narrow, the pressure loss tends to increase and it becomes difficult to ensure the ventilation property. If the slit depth ratio is more than 95%, it is difficult to ensure the strength of the porous member and there is a fear that the porous member becomes vulnerable to breakage. Setting the slit depth ratio within the above-described range makes it possible to ensure an adequate ventilation property and maintain the strength of the porous member.

It is preferred that the slits are formed into a shape intersecting with the longitudinal direction of the strip-shaped porous member, and it is more preferred that an intersection angle between a slit and the longitudinal direction (either an acute angle or a right angle) is 50-70°. When the slits are formed into a shape intersecting with the longitudinal direction of the strip-shaped porous member, in the heat and moisture exchange material formed by coiling the porous member the slits become flow paths communicating with both axial ends of the heat and moisture exchange material. Thus, when the intersection angle is less than 50°, there is a fear that the pressure loss may increase and the ventilation property may be degraded. Further, when the intersection angle is more than 70°, there is a fear that the moisture retention capability may be degraded. By setting the intersection angle to 50-70°, it is possible to achieve an excellent moisture retention capability while reducing an increase in pressure loss to a minimum.

The slits are preferably formed into a zigzag shape having a bend or curve, and more preferably formed into a zigzag shape having a plurality of bends or curves. Forming a bend or curve in each slit makes it possible for a single heat and moisture exchange material to achieve advantages comparable to those obtained by stacking a plurality of heat and moisture exchange materials in which straight-shaped slits are formed, and thus makes it possible to achieve improvements in moisturizing capability and moisture retention capability while suppressing a complexity in manufacturing process and a degradation in ventilation property to a minimum. From the viewpoint of ensuring the ventilation property, the bend or curve is preferably formed into a shape having an obtuse angle and, in each section of a slit divided by the bend or curve, an intersection angle between the section and the longitudinal direction of the porous member is preferably 50-70°.

A water absorption ratio of the porous member is preferably 500% or higher, and more preferably 1000% or higher. The water absorption ratio means a rate of increase in weight when a porous member is immersed to absorb water, and is defined as a ratio $W/W_0$ (%) of a weight after immersion W to a dry weight $W_0$. When the porous member of which the heat and moisture exchange material is made has a water absorption ratio of 500% or higher, a heat and moisture material smaller than conventional ones can exhibit a moisture retention capability equivalent to or higher than that of the conventional ones, thereby enabling miniaturization of the heat and moisture exchange material, and by extension, of the whole of the heat and moisture exchanger. Further, miniaturization of the heat and moisture exchanger makes it possible to improve easiness in handling and reduce a burden on a patient. Further, because the porous member alone can exhibit an adequate moisture retention capability, it is possible to reduce an amount of a hygroscopic substance (for example, calcium chloride, a glycol, an acrylic acid compound and the like) or stop using the hygroscopic substance at all, and thereby it is possible to reduce the manufacturing cost.

It is preferred that the above-described porous member is made of a cellulose sponge. A cellulose sponge has a high heat resistance compared to other resins (such as urethane resins), is stable in an ordinary organic solvent and excellent in water absorption capability and, therefore, makes it possible to provide a heat and moisture exchanger having a high moisture retention capability and an excellent durability. Further, the cellulose sponge is also preferred from the viewpoint of environmental protection because the cellulose sponge consisting of plant-derived fibers is biodegradable and does not emit any toxic gas at the time of combustion.

The heat and moisture exchanger is suitable as a heat and moisture exchanger connected to a ventilator for which excellent moisturizing capability and high ventilation property are required.

The structure of the heat and moisture exchanger makes it possible to provide a heat and moisture exchanger with low pressure loss and high ventilation property, because the slits formed on the porous member serve as flow paths for exhalation and inhalation. Further, because the amount of pressure loss, the moisture retention capability and the moisturizing capability can be controlled by changing the shape of the slits, it is possible to meet a wide variety of performance requirements with flexibility. In particular, controlling the shape of the slits makes it possible to maintain a high ventilation property and exhibit an excellent moisturizing capability, and thereby it is possible to reduce a burden on a patient. Further, because such a heat and moisture exchanger is configured with a relatively simple structure, it can be manufactured at low cost and is excellent in productivity.

Further, using a porous member having a water absorption ratio of 500% or higher or a porous member made of a cellulose sponge makes it possible to provide a heat and moisture exchanger having an excellent moisture retention capability even without any hygroscopic substance, and thereby it is possible to reduce manufacturing cost and miniaturize the heat and moisture exchanger. In particular, using a porous member made of a cellulose sponge makes it possible to provide a heat and moisture exchanger having an excellent durability with small environmental load at low cost.

Hereinafter, examples will be explained with reference to the accompanying drawings.

FIG. 1 shows a heat and moisture exchanger according to one example. In FIG. 1, (A)-(C) depict a strip-like porous member 1, (A) is a diagrammatic oblique view of porous member 1, (B) is a partially enlarged oblique view of porous member 1, and (C) is a partially enlarged plan view of porous member 1. With respect to axes shown in (A)-(C) of FIG. 1, x-axis, y-axis and z-axis correspond to a longitudinal direction of porous member 1, a width direction and a thickness direction, respectively. As shown in FIG. 1 (B), a plurality of slits 2 having a depth D are formed on one surface of strip-like porous member 1 having a thickness T, and each of slits 2 is formed in a zigzag shape in which a plurality of straight parts 3 are connected via bends 4. Every straight part 3 that forms slit 2 intersects with the longitudinal direction of porous member 1 at an intersection angle $\alpha=60°$, and every bend 4 has an angle of 120°.

Figure 2:
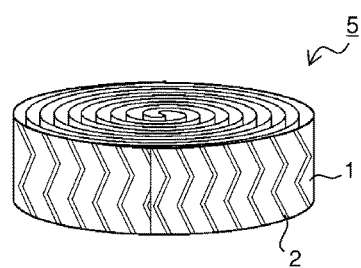
FIG. 2 is a diagrammatic oblique view showing a heat and moisture exchange material including the porous member of FIG. 1.

FIG. 2 depicts a heat and moisture exchange material 5 formed by coiling the strip-shaped porous member 1 into a spirally-wound shape. In heat and moisture exchange material 5, as shown in FIG. 2, porous member 1 is coiled into a spirally-wound shape so that the slits 2 face radially outward.

Figure 3:
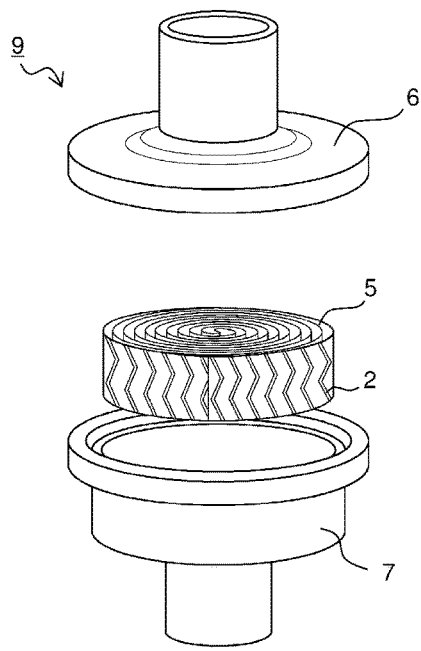
FIG. 3 is a diagrammatic sketch showing an example of heat and moisture exchanger including the heat and moisture exchange material of FIG. 2.
Figure 3:
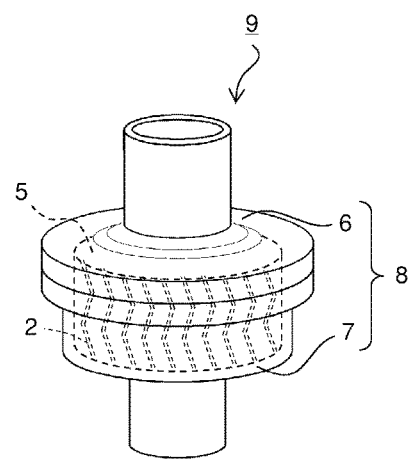
Figure 3:
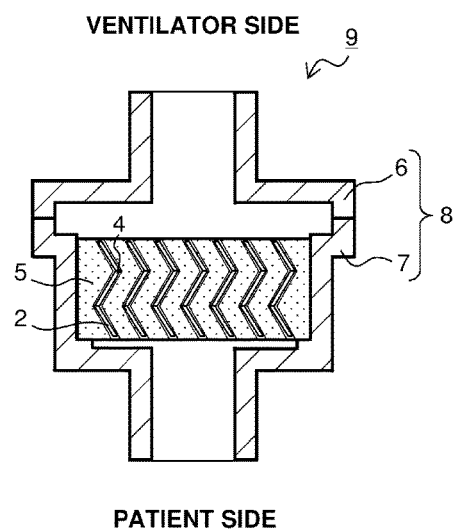

FIG. 3 depicts a heat and moisture exchanger 9 in which heat and moisture exchange material 5 is accommodated in a housing 8 comprising a lid member 6 and a casing member 7. FIG. 3 (A) is a diagrammatic sketch showing a structure of heat and moisture exchanger 9, and FIG. 3 (B) is a diagrammatic oblique view of heat and moisture exchanger 9. As shown in FIGS. 3 (A) and (B), heat and moisture exchanger 9 is assembled by accommodating heat and moisture material 5 in casing member 7 and thereafter fastening lid member 6 to casing member 7. The method of fastening lid member 6 to casing member 7 is not particularly limited and can be any of, for example, a method of heat-welding mating parts of both members using ultrasonic welding method or the like, a method of adhering both members, a fastening method using a fastening member such as bolt, a method of engaging a lug formed in one member with a groove formed in another member, and a method of fastening a female screw part formed in one member to a male screw part formed in another member. From the viewpoints of ensuring hermeticity and ease of handling, the preferred method among others is a method of fastening both members by adhesion or heat-welding.

FIG. 3 (C) is a diagrammatic vertical cross-sectional view of heat and moisture exchanger 9. As shown in FIG. 3 (C), in heat and moisture exchanger 9, slits 2 that are formed on heat and moisture exchange material 5 serve as flow paths for exhalation and inhalation, thereby reducing pressure loss and ensuring ventilation property. Further, because one or more bends are formed in each slit 2, moisture contained in inhalation air is partially absorbed in heat and moisture exchange material 5 when the inhalation air passes through the bend, and therefore heat and moisture exchange material 5 exhibits an excellent moisture retention capability.

Figure 4:
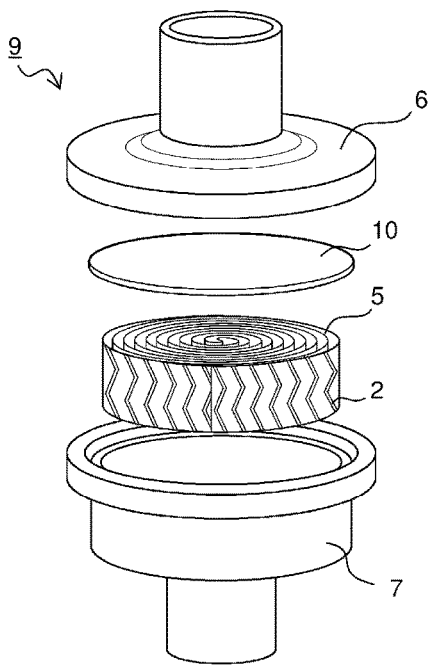
FIG. 4 is a diagrammatic sketch showing another example of heat and moisture exchanger including the heat and moisture exchange material of FIG. 2.
Figure 4:
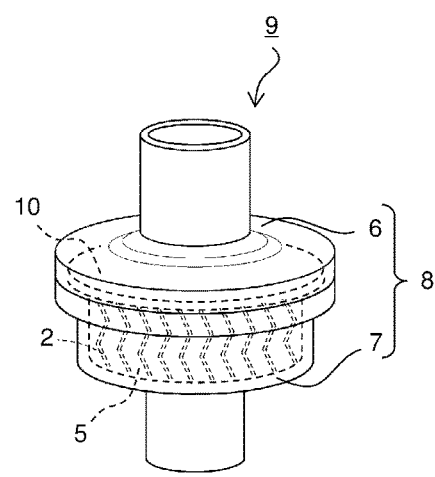
Figure 4:
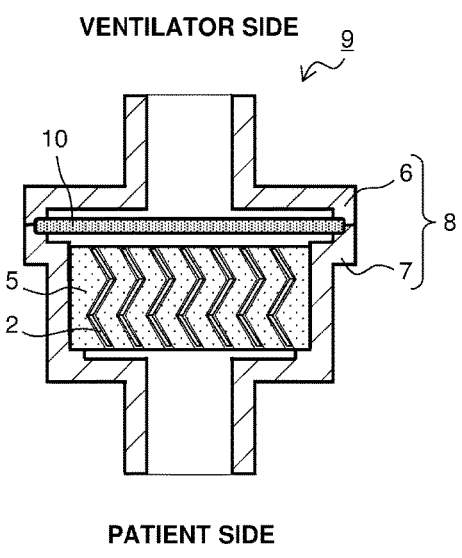

FIG. 4 depicts another example of heat and moisture exchanger 9 in which heat and moisture exchange material 5 is accommodated in a housing 8 comprising a lid member 6 and a casing member 7. FIG. 4 (A) is a diagrammatic sketch showing a structure of heat and moisture exchanger 9, FIG. 4 (B) is a diagrammatic oblique view of heat and moisture exchanger 9, and FIG. 4 (C) is a diagrammatic vertical cross-sectional view of heat and moisture exchanger 9. The explanation of the parts similar to those shown in FIG. 3 will be omitted by assigning the same symbols as FIG. 3. The example shown in FIG. 4 is very similar to FIG. 3. However, in the example of FIG. 4, in addition to heat and moisture exchanger 5, a bacteria filter 10 is positioned in housing 8 on lid member 6 side (ventilator side) to maintain the cleanliness of inhalation air.

Figure 5:
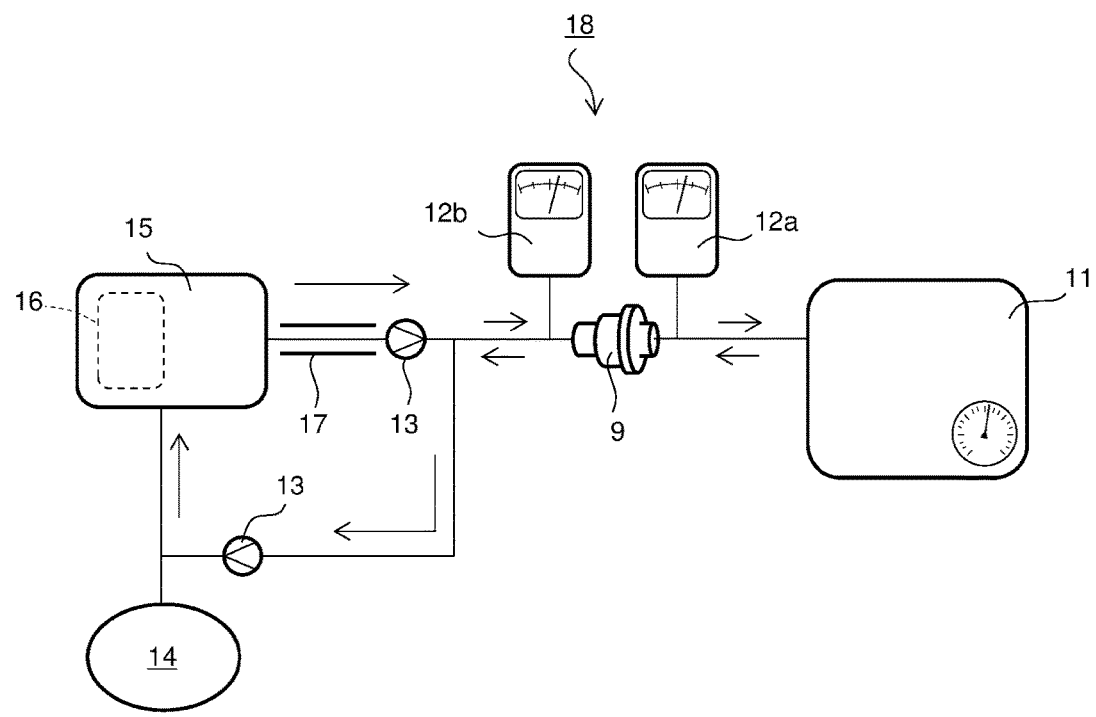
FIG. 5 is a diagrammatic circuit diagram showing a circuit used in a performance test of heat and moisture exchanger.

FIG. 5 is a diagrammatic circuit diagram showing a performance test circuit 18. In circuit 18 of FIG. 5, an opening of heat and moisture exchanger 9 is in communication with a ventilator 11 having a pressure gauge. The other opening of heat and moisture exchanger 9 is in communication with a test lung 14, and the exhalation air from test lung 14 is brought back to heat and moisture exchanger 9 through an active humidifier 15 having a moisturizing chamber 16. To prevent backflow, check valves 13 are positioned at portions of a portion between heat and moisture exchanger 9 and test lung 14 and a portion between active humidifier 15 and heat and moisture exchanger 9. Further, to maintain air flow temperature, a heat wire 17 is provided at the flow path on the exit side of active humidifier 15. Furthermore, a thermo-hygrometer 12a is provided on ventilator 11 side of an opening of heat and moisture exchanger 9, and a thermo-hygrometer 12b on patient side (test lung 14 side), respectively. Arrows in FIG. 5 show the air-flowing direction in circuit 18.

Figure 6:
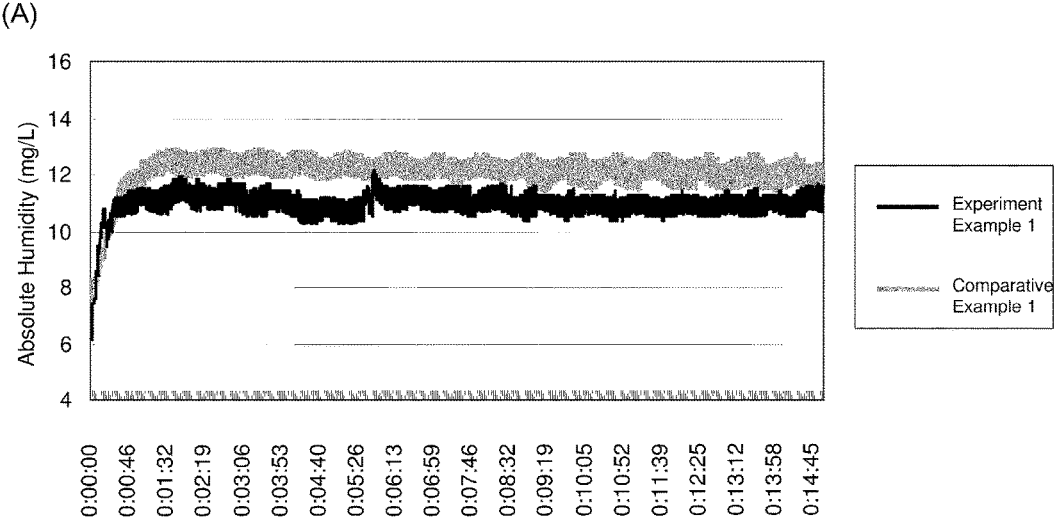
FIG. 6 is a diagram showing a result of performance test of heat and moisture exchanger.
Figure 6:
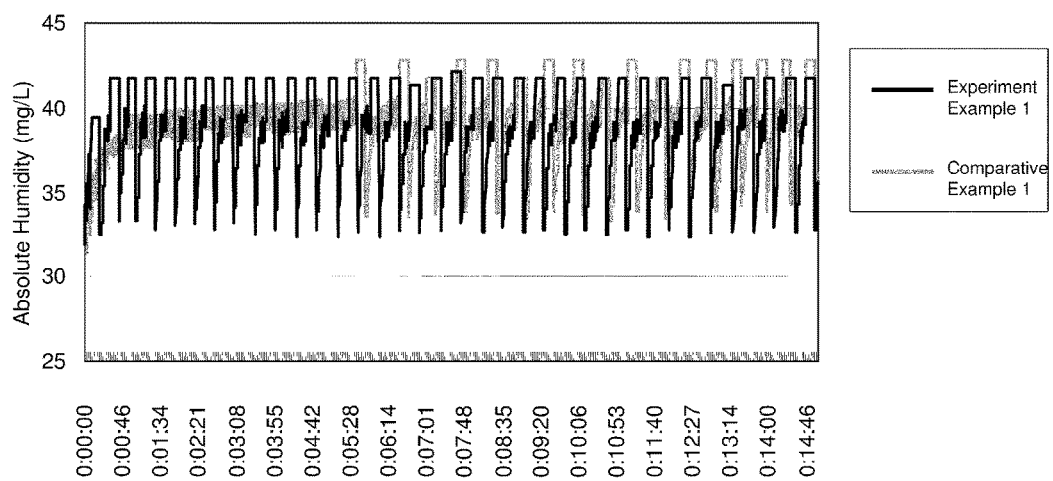

FIG. 6 and Table 1 show the result of performance test of heat and moisture exchanger 9 carried out by using performance test circuit 18 of FIG. 5. FIG. 6 (A) is a diagram showing a measurement result of changes in absolute humidity over time by thermo-hygrometer 12a on ventilator 11 side, and FIG. 6 (B) shows a measurement result of changes in absolute humidity over time by thermo-hygrometer 12b on patient side (test lung 14 side). In Experiment Example 1, a cellulose sponge having a water absorption ratio of 2554% was used as a material of the porous member used for heat and moisture exchanger 9, and in Comparative Example 1, a commercially available heat and moisture exchanger was used in which a heat and moisture exchange material formed by coiling a corrugated paper in a spirally-wound shape is provided. Referring to FIG. 6 (A), on the ventilator side the absolute humidity of Experiment Example 1 is lower than that of Comparative Example 1, showing that heat and moisture exchanger 9 has an excellent moisture retention capability in comparison with the conventional one. Further, referring to FIG. 6 (B) and Table 1, the performances in patient-side humidity and airway pressure are comparable to Comparative Example 1, indicating that performances equivalent to or higher than those of conventional ones are obtained while achieving reduction of the volume of casing by 24% or more.

TABLE 1

| | Porous member [heat and moisture exchange material] | | | | | Housing | | | Heat and moisture exchange material | | Pressure in airway (cm H₂O) | | |
|---|---|---|---|---|---|---|---|---|---|---|---|---|---|
| | Length in longitudinal direction (mm) | Length in width direction (mm) | Thickness T (mm) | Slit depth D (mm) | Slit depth ratio D/T (%) | Water absorption ratio (%) | Internal height of casing (cm) | Diameter (cm) | Volume (cm³) | Sponge weight at the start (g) | Absorbed moisture weight after 2 hours (g) | at the start | 1 hour after the start | 2 hours after the start |
| Experiment Example 1 | 510 | 15.0 | 5.0 | 3.0 | 0.60 | 2554 | 1.50 | 4.7 | 26.0 | 2.2094 | 0.9877 | 27.6 | 30.3 | 30.8 |
| Comparative Example 1 | 4972 | 15.4 | 0.18 | 0.13 | 0.72 | 160 | 1.75 | 5.0 | 34.4 | — | 0.9904 | 30.2 | 31.3 | 31.4 |

Figure 7:
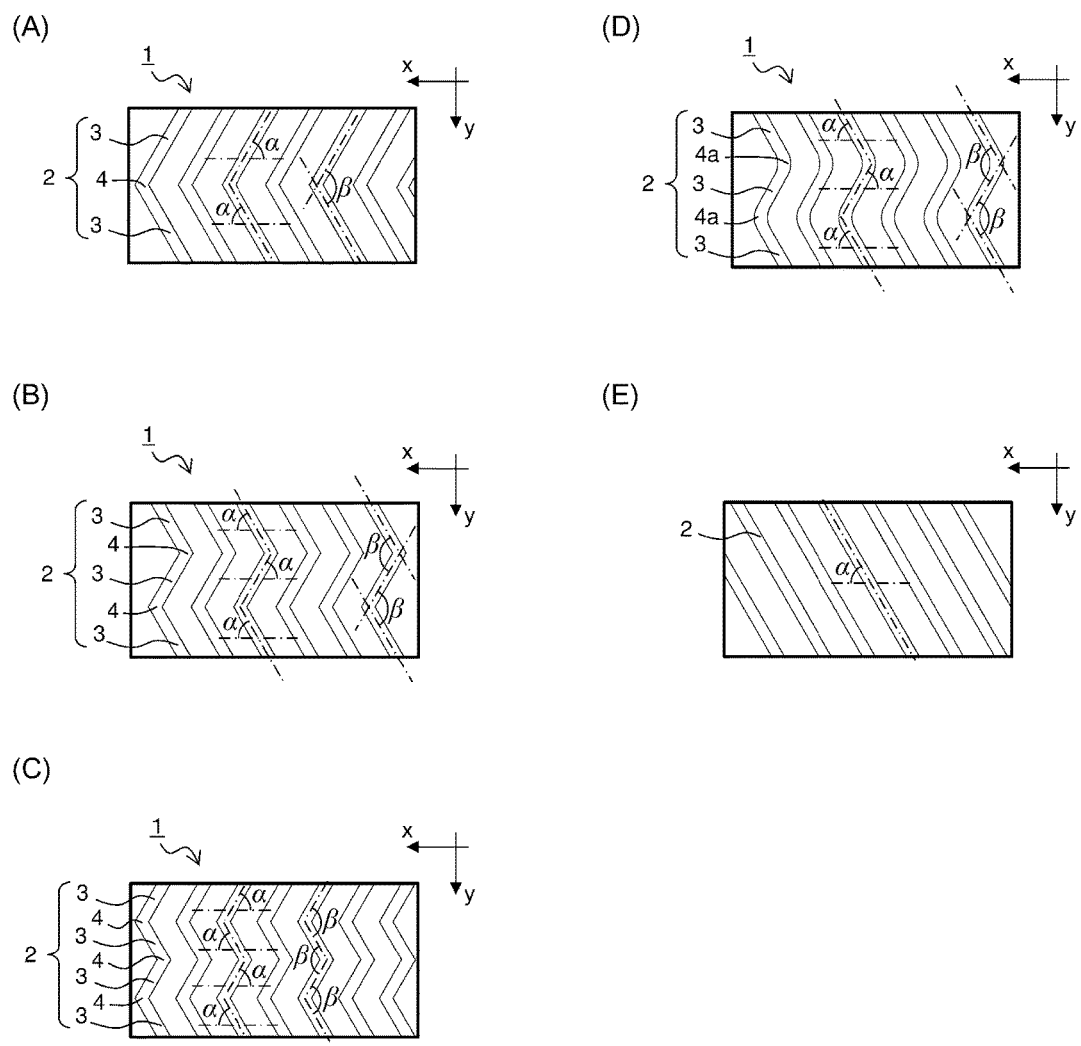
FIG. 7 is a partially enlarged plan view showing examples of slit shape.

FIG. 7 shows examples of shape variations of slit 2. In FIG. 7, each of (A)-(E) is a partially enlarged plan view of porous member 1, (A)-(C) show slits 2 formed into a zigzag shape having one or more bends 4, (D) shows slits 2 formed into a zigzag shape having curves 4a, and (E) shows slits formed into a straight shape. With respect to axes shown in FIG. 7, as with the case of FIG. 1 (C), x-axis and y-axis correspond to a longitudinal direction and a width direction of porous member 1, respectively. As the Figure indicates, the shape of slit 2 is not particularly limited, and any suitable shape can be applied thereto, as appropriate, in accordance with the use and performance required.

Table 2 shows a result of performance test of heat and moisture exchangers, each using one of porous members shown in FIG. 7 (A)-(C). According to Table 2, the absolute humidity in exhalation air (the absolute humidity on ventilator side) decreased when the number of bends 4 formed in a slit 2 is 2 or more, indicating that the moisture retention capability of heat and moisture exchanger material improves as the number of bends 4 increases.

TABLE 2

| | Porous member [Heat and moisture exchange material] | | | | | | | | | Experiment Result (0.5 hours after ventilation starts) | |
|---|---|---|---|---|---|---|---|---|---|---|---|
| | Length in longitudinal direction (mm) | Length in width direction (mm) | Thickness T (mm) | Slit depth D (mm) | Slit depth ratio D/T (%) | Number Of bends | Number of slit steps | Slit shape | Filter | Pressure in airway (cm H₂O) | Absolute Humidity in exhalation air (mg/L) |
| Experiment Example 2 | 510 | 15.0 | 5.0 | 3.0 | 60% | 1 | 2 | FIG. 7 (A) | None | 27.2 | 13.0-14.0 |

TABLE 2-continued

| | Porous member [Heat and moisture exchange material] | | | | | | | | Experiment Result (0.5 hours after ventilation starts) | |
|---|---|---|---|---|---|---|---|---|---|---|
| | Length in longitudinal direction (mm) | Length in width direction (mm) | Thickness T (mm) | Slit depth D (mm) | Slit depth ratio D/T (%) | Number Of bends | Number of slit steps | Slit shape | Filter | Pressure in airway (cm H$_2$O) | Absolute Humidity in exhalation air (mg/L) |
| Experiment Example 3 | 510 | 15.0 | 5.0 | 3.0 | 60% | 2 | 3 | FIG. 7 (B) | None | 27.0 | 11.0-12.0 |
| Experiment Example 4 | 510 | 15.0 | 5.0 | 3.0 | 60% | 3 | 4 | FIG. 7 (C) | None | 27.0 | 11.0-12.0 |

Figure 8:
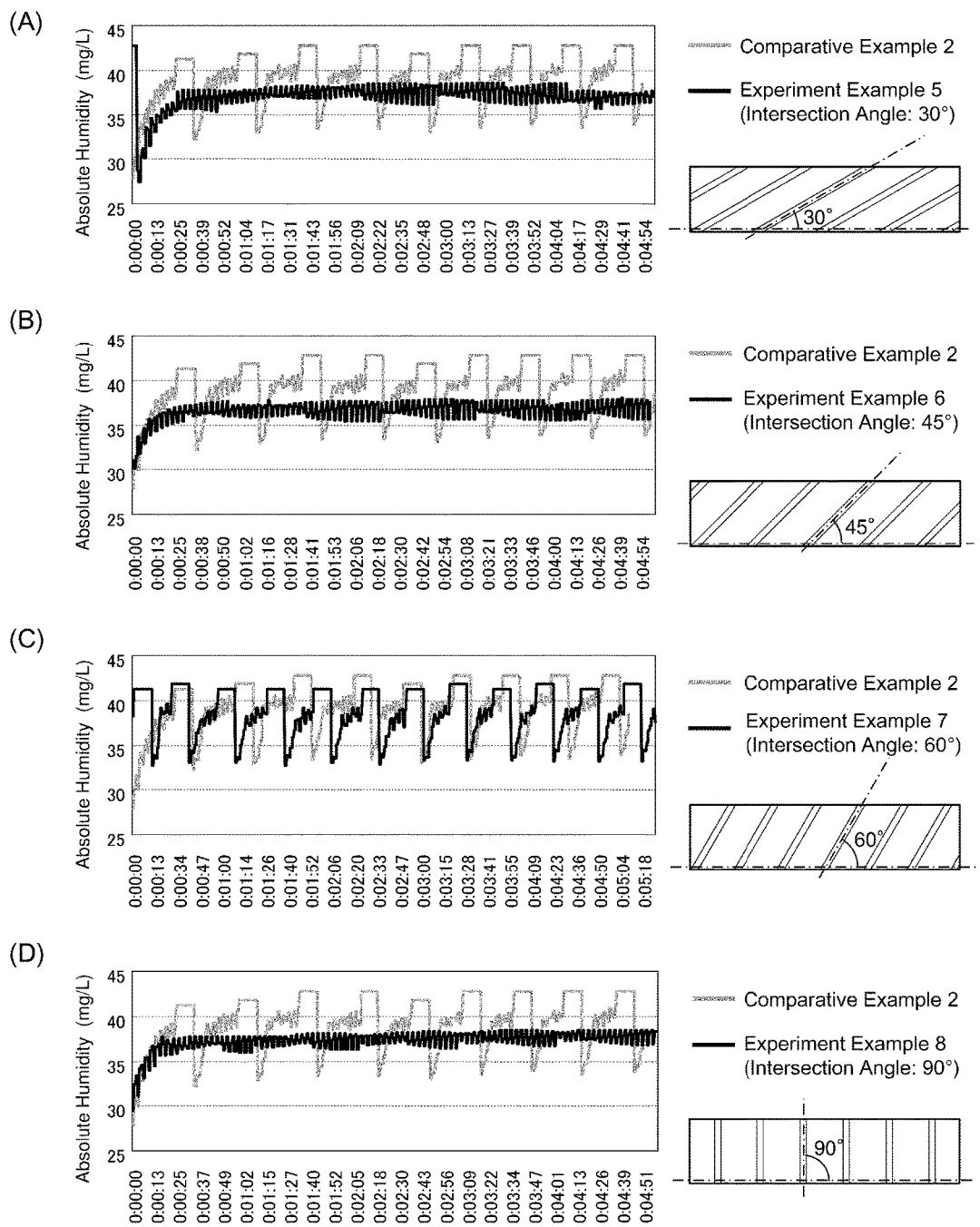
FIG. 8 is another diagram showing a result of performance test of heat and moisture exchanger.

FIG. 8 shows a result of performance test of heat and moisture exchanger having a heat and moisture exchange material with straight slits under several conditions where the slit angle is changed. In Experiment Examples 5-8 of FIG. 8, the porous member has a length of 540 mm, a width of 7 mm and a thickness of 4.5 mm. The humidity in the circuit on the patient side was measured under different conditions where the intersection angle was set to 30°, 45°, 60° or 90°. In Comparative Example 2, a commercially available heat and moisture exchanger having a heat and moisture exchange material formed by coiling a corrugated paper is used. FIG. 8 indicates that the absolute humidity on the patient side became highest and the moisturizing capability was thus most excellent when the intersection angle between the longitudinal direction of the porous member and the slit is 60°, namely, when the intersection angle is within a range of 50-70°.

Figure 9:
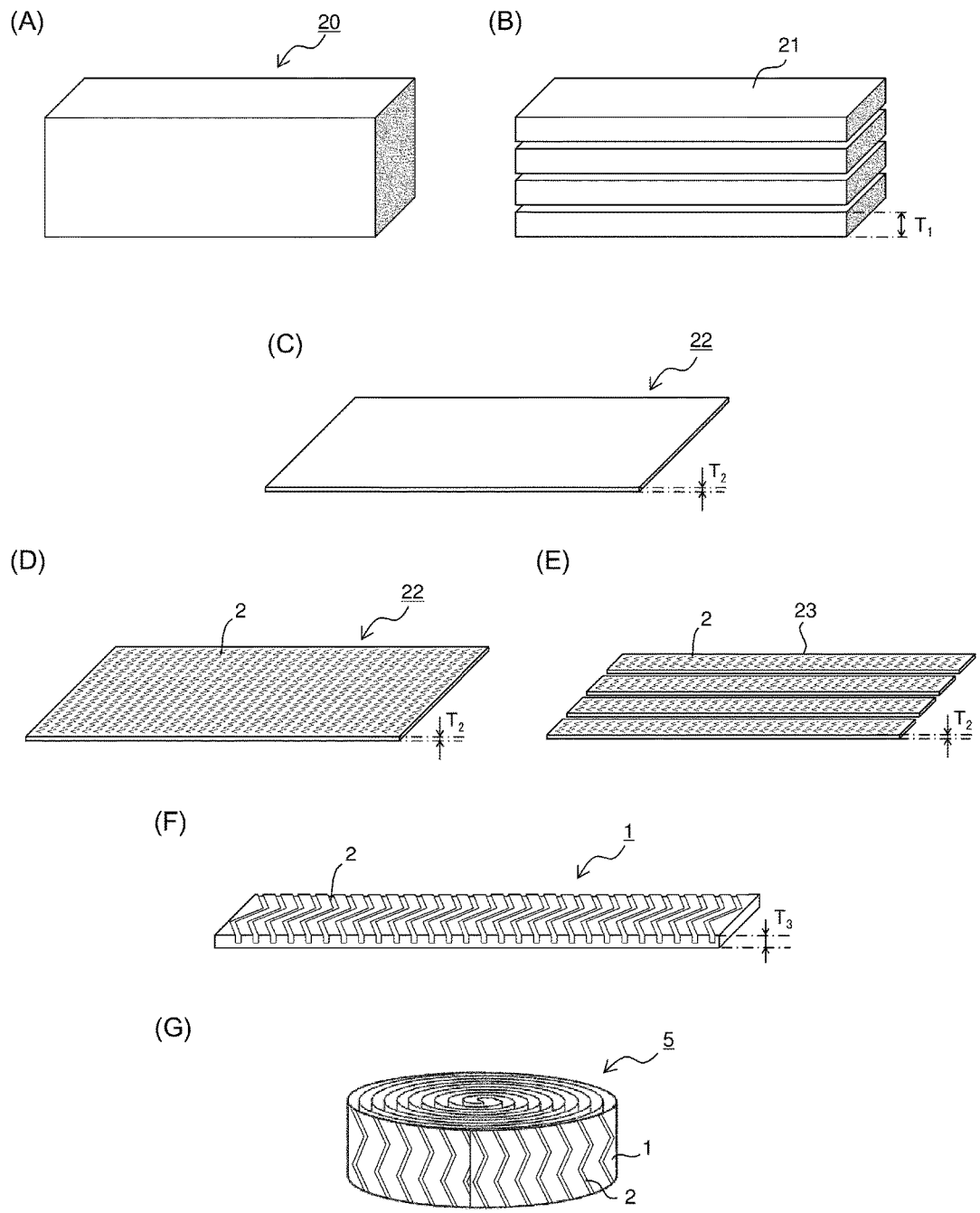
FIG. 9 is a diagrammatic sketch showing an example of process for producing heat and moisture exchanger.

FIG. 9 is a diagrammatic sketch showing an example of a method of producing a heat and moisture exchange material used in a heat and moisture exchanger. FIG. 9 (A) depicts a raw material of cellulose sponge 20 which is a porous material, and by performing a slice process for slicing this raw material 20, a cellulose sponge sheet 21 having a thickness T$_1$ is formed as shown in FIG. 9 (B). Next, by performing a heat-compression process for drying and heat-compressing this cellulose sponge sheet 21, a heat-compressed sheet 22 having a thickness T$_2$ is formed as shown in FIG. 9 (C). Then, by performing a slit-forming process for forming slits on a surface of heat-compressed sheet 22 having a thickness T$_2$, slits 2 are formed on the surface of heat-compressed sheet 22 as shown in FIG. 9 (D). From the viewpoint of ease of processing, the compression ratio T$_2$/T$_1$ (%) of sheet 22 is preferably in a range from 5% to 30%.

After forming the slits, by performing a cutting process for cutting heat-compressed sheet 22, a heat-compressed porous member 23 is formed as shown in FIG. 9 (E). Thereafter, by performing a moisturizing process for moisturizing and enlarging heat-compressed porous member 23, a porous member having a thickness T$_3$ and having a plurality of slits on its surface with depth D is formed as shown in FIG. 9 (F). Then, by performing a coiling process of coiling porous member 1 in a spirally-wound shape with slits 2 facing radially outward, heat and moisture exchange material 5 is obtained as shown in FIG. 9 (G). The decompression ratio T$_3$/T$_1$(%) of the thickness T$_3$ of porous member 1 to the thickness T$_1$ of sheet 21 is preferably in a range from 50% to 100%.

According to the production method shown in FIG. 9, because the heat-compressed sheet 22 is dried and compressed in the slit-forming process, surface processing can be performed easily and it is thus possible to form uniform slits with high precision. As a result, it is possible to provide a heat and moisture exchanger having small pressure loss that lowers a burden on a patient. For example, the heat and moisture exchanger 5 (porous member 1) which is made of cellulose sponge and is used in Experiment Example 1, as shown in the above-described FIG. 6 and Table 1, is produced by the method shown in FIG. 9. More specifically, with respect to the production conditions, the thickness T$_1$ of sheet 21 was 7.0 mm, the thickness T$_2$ of heat-compressed sheet 22 was 1.0 mm, the thickness of porous member 1 after the humidifying process was 5.0 mm, the compression ratio T$_2$/T$_1$ of sheet 22 was 14.3%, and the decompression ratio T$_3$/T$_1$ of porous member 1 was 71.4%.

INDUSTRIAL APPLICABILITY

The structure of the heat and moisture exchanger can be applied to any types of heat and moisture exchanger, and particularly, can be preferably applied to a heat and moisture exchanger connected to a ventilator for which excellent moisturizing capability and high ventilation property are required.

The invention claimed is:

1. A heat and moisture exchanger comprising: a heat and moisture exchange material formed into a spirally-wound shape with a plurality of slits facing radially outwardly from a central axis extending through the spirally-wound shape by coiling a substantially flat strip-shaped porous member having said slits that are located between opposed surfaces of the porous member and arranged along a longitudinal direction of said porous member; and a housing that accommodates said heat and moisture exchange material.

2. The heat and moisture exchanger according to claim 1, wherein said slits are formed on a surface of said porous member at a slit depth ratio of 40-95%.

3. The heat and moisture exchanger according to claim 2, wherein said slits are formed in a shape intersecting with said longitudinal direction.

4. The heat and moisture exchanger according to claim 2, wherein said slits are formed in a zigzag shape.

5. The heat and moisture exchanger according to claim 2, wherein a water absorption ratio of said porous member is 500% or higher.

6. The heat and moisture exchanger according to claim 2, wherein said porous member is made of a cellulose sponge.

7. The heat and moisture exchanger according to claim 1, wherein said slits are formed in a shape intersecting with said longitudinal direction.

8. The heat and moisture exchanger according to claim 7, wherein said slits are formed in a zigzag shape.

9. The heat and moisture exchanger according to claim 7, wherein a water absorption ratio of said porous member is 500% or higher.

10. The heat and moisture exchanger according to claim 7, wherein said porous member is made of a cellulose sponge.

11. The heat and moisture exchanger according to claim 1, wherein said slits are formed in a zigzag shape.

12. The heat and moisture exchanger according to claim 11, wherein a water absorption ratio of said porous member is 500% or higher.

13. The heat and moisture exchanger according to claim 11, wherein said porous member is made of a cellulose sponge.

14. The heat and moisture exchanger according to claim 1, wherein a water absorption ratio of said porous member is 500% or higher.

15. The heat and moisture exchanger according to claim 1, wherein said porous member is made of a cellulose sponge.

16. The heat and moisture exchanger according to claim 1, wherein said heat and moisture exchanger is used with a ventilator connected thereto.

17. A heat and moisture exchanger comprising: a heat and moisture exchange material formed into a spirally-wound shape with a plurality of slits facing radially outwardly from a central axis extending through the spirally-wound shape by coiling a substantially flat strip-shaped porous member having said slits that are located between opposed surfaces of the porous member and arranged along a longitudinal direction of said porous member; and a housing that accommodates said heat and moisture exchange material, wherein said slits are formed in the shape intersecting with said longitudinal direction at an intersection angle of 50-70°.

* * * * *